Figure 1:
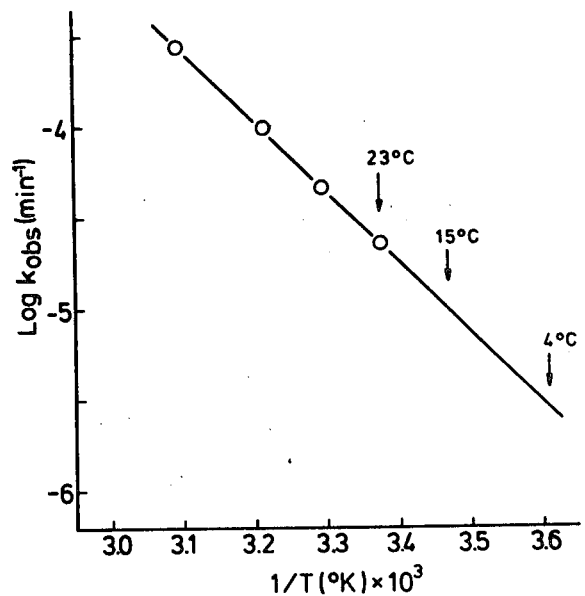

United States Patent [19]

Thorbek et al.

[11] Patent Number: 4,482,722

[45] Date of Patent: Nov. 13, 1984

[54] ESTER OF METRONIDAZOLE WITH N,N-DIMETHYLGLYCINE AND ACID ADDITION SALT THEREOF

[75] Inventors: Pia Thorbek; Hans Bundgaard, both of Horsholm; Claus Larsen, Lejre, all of Denmark

[73] Assignee: A/S Dumex (Dumex Ltd.), Copenhagen, Denmark

[21] Appl. No.: 502,210

[22] Filed: Jun. 8, 1983

[30] Foreign Application Priority Data

Jun. 11, 1982 [DK] Denmark .............................. 2643/82

[51] Int. Cl.$^3$ .......................................... C07D 233/95
[52] U.S. Cl. ................................................. 548/338
[58] Field of Search ......................................... 548/338

[56] References Cited

U.S. PATENT DOCUMENTS 2,944,061  7/1960  Jacob et al. .......................... 548/338
3,803,165  4/1974  Gamaliel et al. ..................... 548/338

Primary Examiner—Robert W. Ramsuer
Attorney, Agent, or Firm—Watson, Cole, Grindle & Watson

[57] ABSTRACT

N,N-dimethylglycine ester of metronidazole, acid addition salt thereof and method of preparing such ester or acid addition salt. The novel compounds exhibit favorable solubility in water and are especially useful for the parenteral treatment of certain anaerobic infections.

2 Claims, 3 Drawing Figures

ESTER OF METRONIDAZOLE WITH N,N-DIMETHYLGLYCINE AND ACID ADDITION SALT THEREOF

BACKGROUND OF THE INVENTION

In the systemic treatment of anaerobic infections a parenteral mode of administration is advantageous for patients who are seriously ill and for whom oral administration is not feasible or may be considered to be insufficiently incisive. Heretofore, a practical way of administering a parenteral dose of metronidazole has not been available since the solubility of metronidazole in an aqueous solution is only about 100 mg/10 ml and a practical dosage unit is in the 500-650 mg/10 ml range. Those skilled in the art recognize the practical advantages of a single injectable dose of below 5 ml as opposed to the large volume of solution which would be needed to administer a 500-650 mg dose of metronidazole in an aqueous solution.

Attempts have been made to improve the solubility of metronidazole in various ways as illustrated by the following examples:

British patent application No. 2,000,025 discloses a method of solubilizing metronidazole in water by mixing it with gentisic acid in a ratio of 1:4.

U.S. Pat. No. 4,032,645 describes solutions of metronidazole in water with N,N-dimethylacetamide/ethanol or propylene glycol/2,2-dimethyl-1,3-dioxolane-4-methanol as co-solvents.

However, these methods have two drawbacks: Firstly, the solubility of metronidazole is only augmented to 500-650 mg/10 ml and secondly both require large amounts of substances that are foreign to the human organism.

Another conceivable solution to the problem is to administer metronidazole in the form of a derivative which has the desired solubility and which, after parenteral administration, is cleaved by the organism to yield metronidazole. Such a derivative could be an ester prepared from a pharmacologically acceptable acid.

Several esters of metronidazole are known. U.S. Pat. No. 2,994,061 describes esters of metronidazole with mono- or di-carboxylic aliphatic or aromatic acids.

U.S. Pat. No. 3,696,116 describes esters of metronidazole with carbamic acid.

British Pat. No. 1,270,810 mentions 4-toluene-sulphonic acid ester of metronidazole as an intermediate product.

German Offenlegungsschrift No. 2,030,314 describes the ester of methane sulphonic acid with metronidazole.

Unfortunately all of these esters are even less soluble in water than metronidazole itself.

Half-esters of metronidazole with dicarboxylic acids are known from Belgian Pat. No. 619672. The sodium salt of the half-ester with succinic acid which is described therein has the required solubility in water. However, the cleavage of the ester in blood serum after parenteral administration is very slow and the compound itself is microbiologically inactive.

U.S. Pat. No. 4,160,827 describes the monoester of phosphoric acid with metronidazole. The salts of this ester with pharmacologically acceptable cations are very soluble in water.

Although this ester may turn out to be a clinically useful prodrug, published data indicate a rather slow rate of conversion to metronidazole in vivo. Furthermore, the bioavailability to rats of metronidazole occurring after administration of the phosphate ester is significantly lower than that obtained with metronidazole at the same dosage level, which indicates the excretion of some unchanged phosphate ester.

A third type of water-soluble ester derivatives is esters with an ionizable amino function in the acid portion. Various amino acid esters have previously been described as water-soluble bioreversible derivatives of drugs containing a hydroxy group, such as oxazepam and lorazepam (Nudelman et al.: J. Pharm. Sci. 63, 1880-1885 (1974)), hydrocortisone (Kawamura et al.: Yakugaku Zasshi 91, 863-870 (1971)) and a pyridazin-3-one derivative (Fogt et al.: J. Med. Chem. 23, 1445-1448 (1980)), but only sparse information is available on their hydrolysis under physiological conditions.

Amino acid esters with metronidazole have been unknown hitherto. However, it has now been found that aminocarboxylic acid esters with metronidazole are soluble in water and that acid addition salts thereof are very soluble in water. In most cases solutions containing more than 20% w/v of such acid addition salts can be obtained.

Table 1 shows the half-lives for the hydrolysis to metronidazole of a series of such metronidazole esters in 80% human plasma (pH 7.4) and in 0.05M phosphate buffer (pH 7.4) at 37° C.

TABLE 1

| Ester | $t_{\frac{1}{2}}$ in human plasma (min) | $t_{\frac{1}{2}}$ in buffer (min) |
|---|---|---|
| N,N—Dimethylglycinate | 12 | 250 |
| Glycinate | 41 | 115 |
| N—Propylglycinate | 8 | 90 |
| 3-Aminopropionate | 207 | 315 |
| 3-Dimethylaminopropionate | 46 | 52 |
| 4-Dimethylaminobutyrate | 334 | 580 |
| 4-Methyl-1-piperazinoacetate | 523 | 1720 |

Table 1 shows the widely differing ability of the various amino acid esters to undergo hydrolysis in human plasma and in buffer.

As will appear from Table 1 the half-life of the 3-dimethylaminopropionate is only slightly shorter in human plasma compared to buffer and whereas the half-life of the 4-dimethylaminobutyrate is relatively much shorter in plasma than in buffer $t_{\frac{1}{2}}$ in plasma is still so long that the 4-dimethylaminobutyrate is unsuited as a prodrug of metronidazole. The same applies to the 4-methyl-1-piperazinoacetate and 3-aminopropionate. The esters derived from N,N-dimethylglycine and N-propylglycine have short half-lives in plasma, and consequently these compounds appear to be suitable candidates as prodrugs of metronidazole.

Selection of the optimum prodrug derivative should take into account several other criteria such as the in vitro stability in bulk form and in aqueous solution, toxicity of both the prodrug and the aminoacid moiety released from the derivative, and the ease of synthesis and purification. Based on these criteria the N,N-dimethylglycine ester of metronidazole and acid addition salts thereof have been found to be very suitable prodrugs of metronidazole.

SUMMARY OF THE INVENTION

The novel compounds of the invention are metronidazole esters having the formula I:

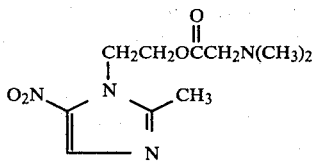

and acid addition salts thereof.

A preferred acid addition salt of the N,N-dimethylglycine ester of the invention is the hydrochloride salt.

The novel compounds of the invention may be prepared (a) by reacting metronidazole having the formula II:

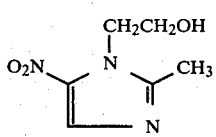

with a halogenoacetyl halide having the general formula III:

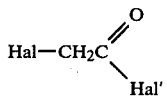

wherein Hal and Hal' each is selected from the group consisting of chloro and bromo atoms to form a compound having the general formula IV:

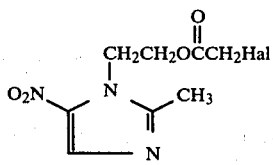

wherein Hal has the meaning defined above, optionally reacting the compound having the general formula IV with an alkali metal iodide dissolved in an organic solvent to form a compound having the formula V:

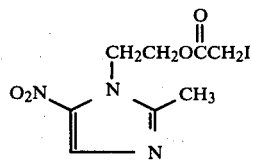

reacting a compound having the formula IV or V with dimethylamine to form a compound having the formula I and optionally converting said compound into an acid addition salt thereof, or (b) esterifying metronidazole having the formula II with N,N-dimethylglycine in the presence of N,N'-dicyclohexylcarbodiimide to form a compound having the formula I and optionally converting said compound into an acid addition salt thereof.

Metronidazole is preferably reacted with the halogenoacetyl halide having the formula III in a suitable solvent, e.g. methylene chloride, and in the presence of about one equivalent of a base, such as pyridine.

The alkali metal iodide used in the preparation of the compound having the formula V is preferably sodium or potassium iodide and the reaction is preferably carried out in acetone.

The reeaction between the compound having the formula IV or V and dimethylamine is preferably carried out in a non-hydroxylic solvent in which the compound having the formula IV or V is soluble, e.g. acetone. The preferred reaction temperature is room temperature or a temperature below room temperature.

The esterification of metronidazole is preferably carried out at room temperature.

The conversion of the ester obtained by methods (a) and (b) into the corresponding acid addition salt is effected with a suitable pharmacologically acceptable acid, e.g. hydrochloric acid.

The solubility in water of the hydrochloride of metronidazole N,N-dimethylglycinate exceeds 50% w/v or 1.7M at 20° C., the pH of the 1–20% w/v solutions being 4.4–4.6. The solubility of metronidazole in aqueous solutions of pH>3 and at 25° C. is 1% w/v or 0.058M.

The effect of temperature on the rate of hydrolysis of metronidazole N,N-dimethylglycinate was studied in 0.05M acetate buffer of pH 4.4 over the temperature range 23°–50° C.

The results obtained are illustrated in FIG. 1 of the drawings. FIG. 1 shows an Arrhenius plot in which the logarithm of the observed pseudo-first-order rate constants has been plotted against the reciprocal of the absolute temperature. Based on the slope of said plot an activation energy of 17.7 kcal mole$^{-1}$ was calculated. Based on said Arrhenius type plot the stability of aqueous solutions of the ester may be predicted at various temperatures.

Thus, the time in which 10% of the ester is degraded ($t_{10\%}$) is found to be 73 h at 23° C., 166 h at 15° C. and 24 days at 4° C. These values are for a pH of 4.4 which corresponds to the value of aqueous solutions of the hydrochloride salt.

Since $t_{10\%}$ for the ester is 73 h at 23° C., the results given in Table 2 indicate that the stability of aqueous solutions of the prodrug ester will only be limited by the potential precipitation of metronidazole formed upon hydrolysis in those cases where the concentration of the ester in aqueous solutions exceeds about 20%.

TABLE 2

Apparent zero-order initial rates of formation of metronidazole (M) from its prodrug and times for M to begin precipitation ($t_{pt}$) from solutions of the hydrochloride of metronidazole N,N—dimethylglycinate as calculated (at 23° C.).

| Concentration of the hydrochloride of metronidazole N,N—dimethylglycinate (mg ml$^{-1}$) | (d[M]/dt)$_i$ (mg ml$^{-1}$h$^{-1}$) | $t_{pt}$ (h) |
|---|---|---|
| 50 | 0.042 | 238 |
| 100 | 0.084 | 119 |
| 200 | 0.168 | 60 |
| 300 | 0.252 | 40 |

The above data indicate that the stability of the product at pH ~4.5 is compatible with its use as a formulation to be reconstituted as a solution within several hours before use.

ANIMAL STUDIES

Figure 3:
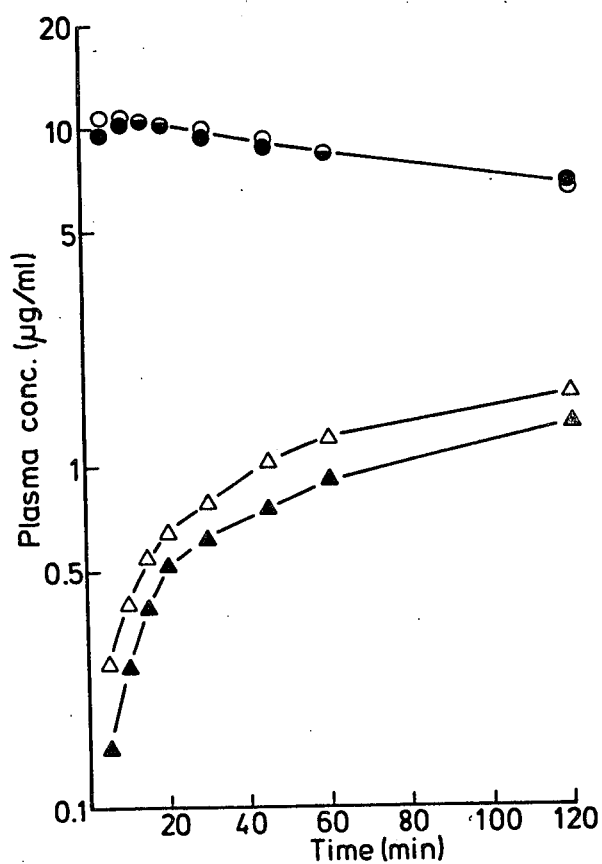
Figure 2:
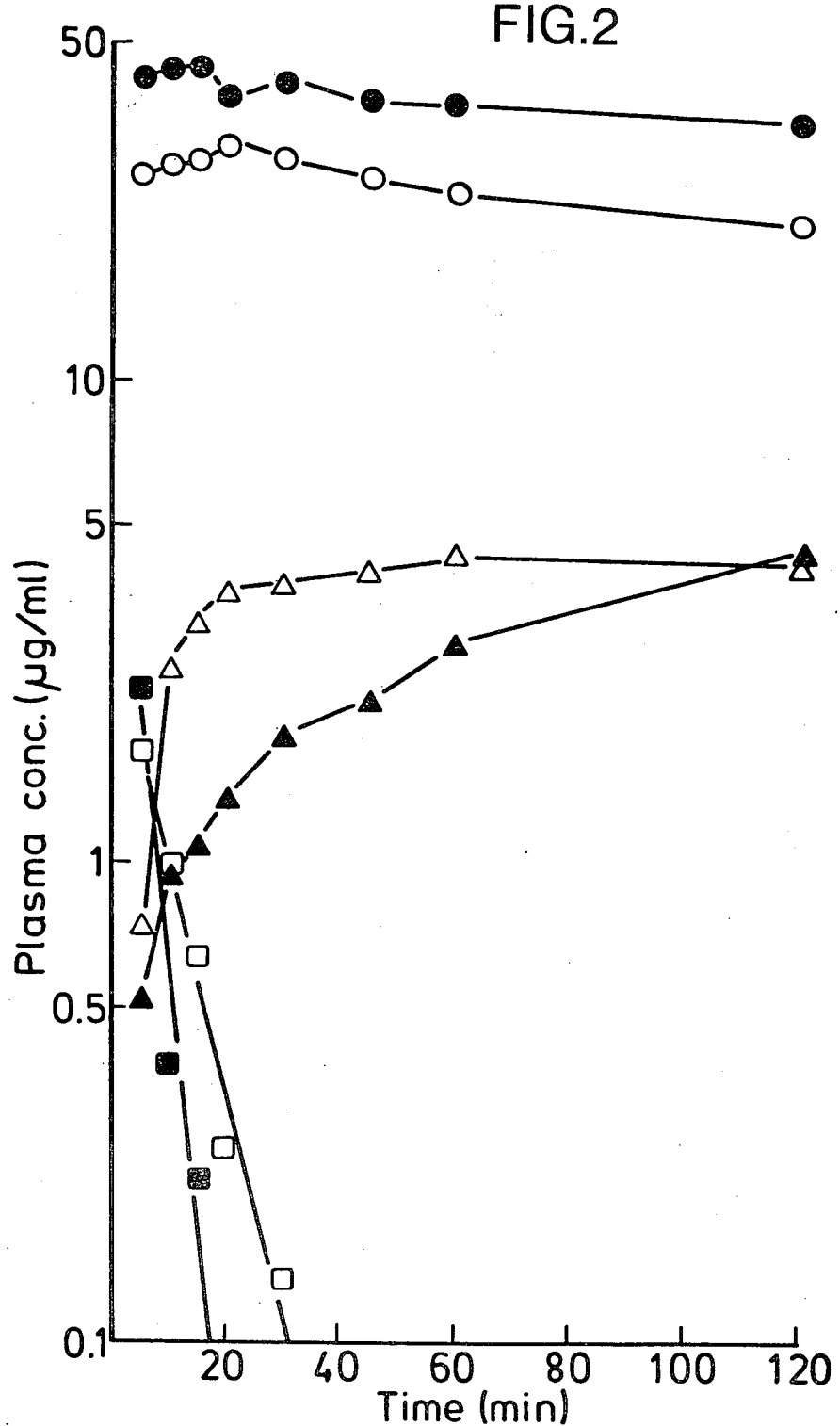

To test the assumption that the N,N-dimethylglycine ester would be a suitable water-soluble prodrug of metronidazole for parenteral administration, metronidazole and its N,N-dimethylglycine ester were given intravenously to two beagle dogs in a cross-over study. FIG. 2 shows plasma concentrations of metronidazole (circles), its major metabolite 1-(2-hydroxyethyl)-2-hydroxymethyl-5-nitroimidazole (triangles) and intact metronidazole N,N-dimethylglycinate (squares) for dog 1 (open symbols) and dog 2 (filled symbols) after intravenous injection of the hydrochloride salt of the ester at a dose of 30 mg/kg of metronidazole equivalents. The plasma concentration versus time data observed after administration of metronidazole are shown in FIG. 3 which shows plasma concentrations of metronidazole (circles) and 1-(2-hydroxyethyl)-2-hydroxymethyl-5-nitroimidazole (triangles) in dog 1 (open symbols) and dog 2 (filled symbols) after intravenous administration of metronidazole at a dose of 10 mg/kg. 2-Methyl-5-nitroimidazole-1-acetic acid, another main metabolite of metronidazole, could not be detected in measurable concentrations in any cases.

The results obtained show that metronidazole N,N-dimethylglycinate is hydrolyzed rapidly in the dogs. The rate of disappearance follows good first-order kinetics as seen from FIG. 2, the half-lives being approximately 3 and 7 min in the two dogs. This observed rate of elimination of the ester may reflect the sum of two processes: conversion to the parent drug and loss of prodrug by other routes.

As noted below the rapid and quantitative formation of metronidazole seen after administration of the ester indicate, however, that the rate of ester disappearance is solely or predominantly due to the hydrolytic conversion. The half-life of hydrolysis in 80% dog plasma at 37° C. in vitro was found to be 25 min. Since the corresponding half-life of hydrolysis in human plasma or blood is 9–12 min, the ester would probably have an even shorter lifetime in humans than that observed in the dogs. Besides, the pattern of metabolite formation following administration of the ester is quite similar to that observed after injection of metronidazole. The hydrochloride of metronidazole N,N-dimethylglycinate is rapidly and completely converted to metronidazole and the metabolism and elimination pattern of the parent compound appear to be similar to that following administration of metronidazole as such.

No signs of pain or local toxicity were observed in the dogs following the intravenous injection of the ester preparation.

The compounds of the present invention may be presented for administration to humans and animals in unit forms intended for parenteral use.

Pharmaceutical dosage unit forms may be prepared in accordance with the following descriptions to provide from 500 mg to 2000 mg of the essential, active ingredient per dosage unit form. Parenteral administration includes intravenous, subcutaneous, intramuscular and similar modes of administration.

Preparations for parenteral administration include sterile solution ready for injection, sterile dry soluble products ready to be combined with a solvent just before use, including hypodermic tablets, sterile suspensions ready for injection, sterile dry insoluble products ready to be combined with a vehicle just before use and sterile emulsions. The preparations may be either aqueous or non-aqueous, composed of pharmaceutically acceptable substances utilized in parenteral preparations including aqueous vehicles, non-aqueous vehicles, antimicrobial agents, isotonic agents, buffers, antioxidants, local anaesthetics, suspending and dispersing agents, emulsifying agents, sequestering or chelating agents and other pharmaceutical necessities.

EXAMPLE 1

Metronidazole N,N-dimethylglycinate hydrochloride

Dimethylamine (38 g, 0.84 mole) is cooled to $-30°$ C., and under stirring added to an ice-cooled solution of metronidazole bromoacetate (116.8 g, 0.40 mole) in dry acetone (750 ml). The mixture is stirred at 5° C. for 3 hours. The dimethylammonium bromide formed is filtered off and the filtrate evaporated in vacuo. The residue is dissolved in 400 ml of methylene chloride and the solution washed with $3 \times 150$ ml of water, dried over magnesium sulphate and evaporated in vacuo. To a solution of the residue in 700 ml of ethyl acetate is added drop-wise while stirring and cooling 3.3M hydrogen chloride in ethyl acetate (123 ml), the stirring being continued for 1 hour at 5° C. after all has been added. The crystalline compound formed is washed with ethyl acetate and recrystallized from methanolethyl acetate-ether.

Yield: 85.5 g (73%), m.p. 210°–211° C.

The metronidazole bromoacetate used as starting material is prepared as follows:

Bromoacetyl bromide (222.0 g, 1.1 mole) is added dropwise under stirring and cooling to a mixture of metronidazole (171.2 g, 1.0 mole) and pyridine (87.0 g, 1.1 mole) in 1500 ml of methylene chloride. The suspension is stirred at room temperature for 3 h, filtered, washed with $3 \times 600$ ml of water, dried over sodium sulphate and evaporated in vacuo. The residue is dissolved in 300 ml of methanol and this solution is added drop-wise to 1200 ml of ice-water with vigorous stirring. After standing at 5° C. for 20 h, the mixture is filtered, giving 217.1 g (74%) of the title compound (m.p. 66°–69° C.).

EXAMPLE 2

Metronidazole N,N-dimethylglycinate hydrochloride

N,N'-Dicyclohexylcarbondiimide (26.6 g, 0.13 mole), N,N-dimethylglycine (12.4 g, 0.12 mole) and metronidazole (17.1 g, 0.10 mole) are added to 200 ml of dry pyridine. After stirring at room temperature for 4 days the mixture is filtered and evaporated to dryness under reduced pressure. The residue is suspended in 300 ml of ethyl acetate, cooled to 5° C. and filtered. To the filtrate is added drop-wise and with stirring 35 ml of 3N hydrogen chloride in ethyl acetate. After standing for 1 h at 5° C. the precipitate formed is filtered, washed with ethyl acetate and recrystallized from 2-methoxyethanol. Yield: 13.6 g (46%); m.p. 210°–211° C. Analysis: Calculated for $C_{10}H_{17}ClN_4O_4$: C, 41.03; H, 5.85; Cl, 12.11; N, 19.14%. Found: C, 41.00; H, 5.96; Cl, 12.25; N, 19.26%. $^1$H-NMR (D$_2$O) δ: 2.88 (3H,s,CCH$_3$); 3.33 (6H,s,N(CH$_3$)$_2$); 4.55 (2H,s,OOCCH$_2$); 4.9–5.2 (4H,m,CH$_2$CH$_2$); 8.32 (1H,s,CH).

EXAMPLE 3

Powder for injections

A sterile solid substance contained in the final vial is prepared from the following types and amounts of sterile materials:

Metronidazole N,N-dimethylglycinate, HCl: 171 g.
Lignocaine hydrochloride: 2 g.

The ingredients are thoroughly mixed and filled into 100 vials, and the vials are sealed. The composition so prepared is suitable for IM injection.

EXAMPLE 4

Powder for injections

A sterile solid substance contained in the final vial is prepared from the following amount of sterile material:
Metronidazole N,N-dimethylglycinate, HCl 171 g.
The substance is filled directly into 100 vials and the vials are sealed.

EXAMPLE 5

Powder for injections

A sterile solid substance distributed in the final vial is prepared from the following amount of material:
Metronidazole N,N-dimethylglycinate, HCl 171 g.
The substance is dissolved in water for injections and the solution sterilized by filtration. The sterile solution is filled into vials, which are freeze dried and finally sealed.

EXAMPLE 6

Powder for injections

A sterile solid substance distributed in the final vial is prepared from the following types and amounts of materials:
Metronidazole N,N-dimethylglycinate, HCl: 171 g.
Mannitol: 5 g.
The ingredients are dissolved in water for injections and the solution sterilized by filtration. The sterile solution is filled into vials, which are freeze dried and finally sealed.

We claim:

1. A metronidazole ester having the formula I:

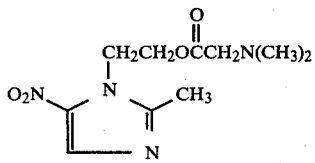

and acid addition salts thereof.

2. Metronidazole N,N-dimethyl glycinate hydrochloride.

* * * * *